(12) United States Patent
Yarger et al.

(10) Patent No.: US 12,728,210 B2
(45) Date of Patent: Sep. 8, 2026

(54) SYSTEMS, APPARATUSES AND METHODS FOR CAPTURING IMAGES OF MEDICAL CONDITION MANAGEMENT EVENTS

(71) Applicant: Becton, Dickinson and Company, Franklin Lakes, NJ (US)

(72) Inventors: Michael D. Yarger, Chapel Hill, NC (US); Andrew L. Richards, Durham, NC (US); Mircea S. Despa, Cary, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 983 days.

(21) Appl. No.: 17/921,731

(22) PCT Filed: Apr. 26, 2021

(86) PCT No.: PCT/US2021/029064
§ 371 (c)(1),
(2) Date: Oct. 27, 2022

(87) PCT Pub. No.: WO2021/222058
PCT Pub. Date: Nov. 4, 2021

(65) Prior Publication Data

US 2023/0166047 A1 Jun. 1, 2023

Related U.S. Application Data

(60) Provisional application No. 63/017,347, filed on Apr. 29, 2020.

(51) Int. Cl.

| | |
|---|---|
| ***A61M 5/315*** | (2006.01) |
| ***A61M 5/20*** | (2006.01) |
| ***A61M 5/32*** | (2006.01) |

(52) U.S. Cl.
CPC ...... *A61M 5/31546* (2013.01); *A61M 5/2033* (2013.01); *A61M 5/3202* (2013.01);
(Continued)

(58) Field of Classification Search
CPC ............ A61M 5/31546; A61M 5/2033; A61M 5/3202; A61M 2005/2013
See application file for complete search history.

(56) References Cited

U.S. PATENT DOCUMENTS

| | | | |
|---|---|---|---|
| 5,902,982 | A | 5/1999 | Lappe |
| 2009/0043253 | A1 | 2/2009 | Podaima |

(Continued)

FOREIGN PATENT DOCUMENTS

| | | | |
|---|---|---|---|
| GB | 701 232 | A | 12/1953 |
| JP | 2008-142565 | A | 6/2008 |

(Continued)

OTHER PUBLICATIONS

International Search Report dated Aug. 17, 2021, which issued in the corresponding PCT Application No. PCT/US2021/029064.

*Primary Examiner* — Dung T Ulsh
(74) *Attorney, Agent, or Firm* — Dickinson Wright PLLC

(57) ABSTRACT

A drug delivery device system with mutable indicia and method for using same are provided. The drug delivery device system includes a syringe and/or syringe components (e.g., needle shield, needle guard), or autoinjector pen, or wearable autoinjector with mutable indicia and a software application for an external device to analyze images of the mutable indicia to automatically determine and record status of the drug delivery device. The mutable indicia or codes on the drug delivery device or its components represent different medical events such as dose completion, dose amount, and safety feature deployment or removal and can be detected by and otherwise logged by the external device.
(Continued)

The external device may execute an application configured to further process data obtained via captured images of mutable indicia and display related information (e.g., fluid remaining in syringe barrel, delivered dose, and so on).

22 Claims, 9 Drawing Sheets

(52) U.S. Cl.
CPC ............... *A61M 2005/2013* (2013.01); *A61M 2205/3584* (2013.01); *A61M 2205/502* (2013.01); *A61M 2205/52* (2013.01)

(56) References Cited

U.S. PATENT DOCUMENTS

| | | | |
|---|---|---|---|
| 2010/0286609 | A1 | 11/2010 | Mahurkar |
| 2013/0345641 | A1 | 12/2013 | Cerman et al. |
| 2015/0209114 | A1 | 7/2015 | Burkholz et al. |
| 2016/0259913 | A1 | 9/2016 | Yu et al. |
| 2017/0286638 | A1 | 10/2017 | Searle et al. |
| 2018/0344941 | A1 | 12/2018 | Cowe |
| 2019/0117888 | A1 | 4/2019 | Burkholz et al. |
| 2019/0341136 | A1 * | 11/2019 | Hopper ................. H04W 4/023 |
| 2021/0196900 | A1 * | 7/2021 | Appy ................. A61M 5/3234 |

FOREIGN PATENT DOCUMENTS

| | | | |
|---|---|---|---|
| JP | 2013-533076 | A | 8/2013 |
| JP | 2013-189241 | A | 9/2013 |
| JP | 2017-510880 | A | 4/2017 |
| JP | 2017-527414 | A | 9/2017 |
| JP | 2017-530772 | A | 10/2017 |
| JP | 2018-530814 | A | 10/2018 |
| JP | 2019-505333 | A | 2/2019 |
| WO | 2005/097232 | A1 | 10/2005 |
| WO | 2014/133053 | A1 | 9/2014 |
| WO | 2020/109888 | A1 | 6/2020 |

* cited by examiner

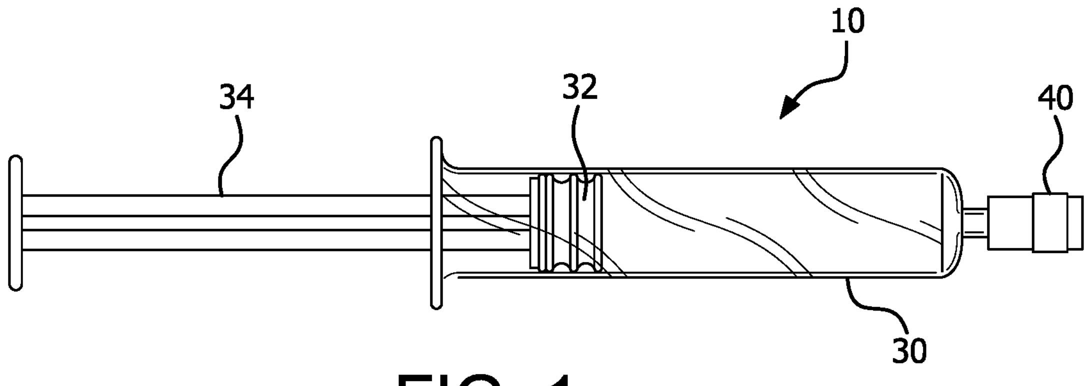
FIG. 1
RELATED ART
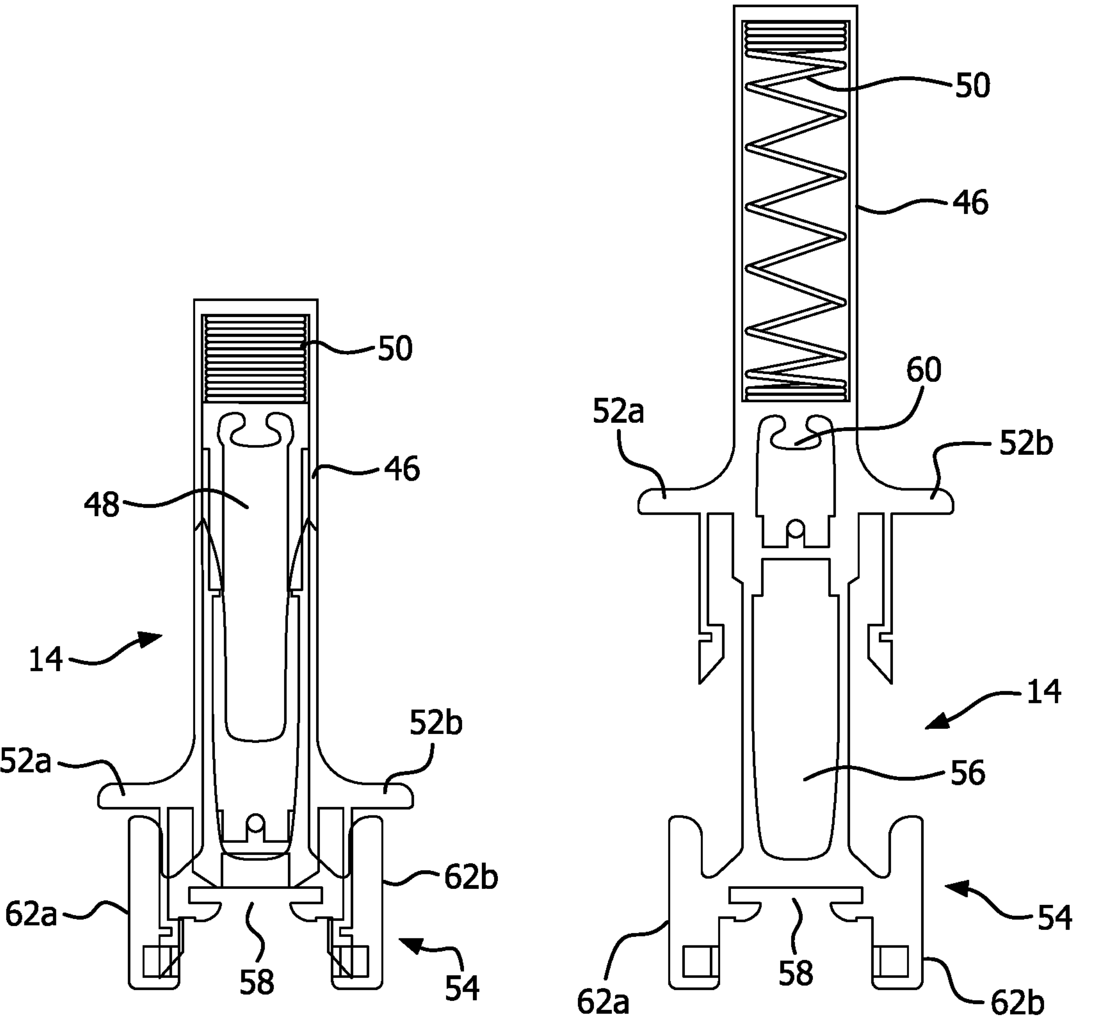
FIG. 2A
RELATED ART
FIG. 2B
RELATED ART

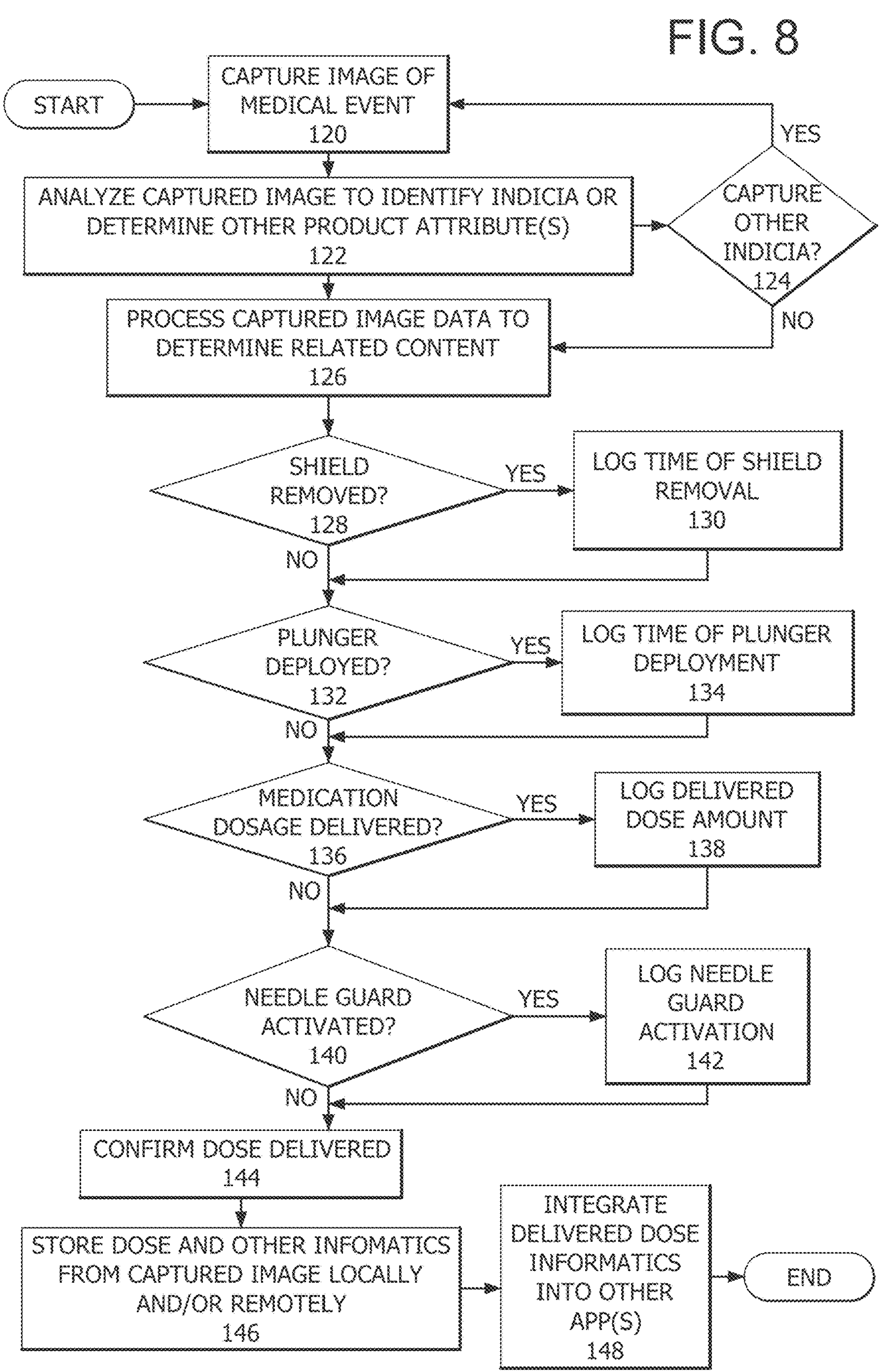
FIG. 8
START
CAPTURE IMAGE OF MEDICAL EVENT 120
ANALYZE CAPTURED IMAGE TO IDENTIFY INDICIA OR DETERMINE OTHER PRODUCT ATTRIBUTE(S) 122
CAPTURE OTHER INDICIA? 124
YES
NO
PROCESS CAPTURED IMAGE DATA TO DETERMINE RELATED CONTENT 126
SHIELD REMOVED? 128
YES
LOG TIME OF SHIELD REMOVAL 130
NO
PLUNGER DEPLOYED? 132
YES
LOG TIME OF PLUNGER DEPLOYMENT 134
NO
MEDICATION DOSAGE DELIVERED? 136
YES
LOG DELIVERED DOSE AMOUNT 138
NO
NEEDLE GUARD ACTIVATED? 140
YES
LOG NEEDLE GUARD ACTIVATION 142
NO
CONFIRM DOSE DELIVERED 144
STORE DOSE AND OTHER INFOMATICS FROM CAPTURED IMAGE LOCALLY AND/OR REMOTELY 146
INTEGRATE DELIVERED DOSE INFORMATICS INTO OTHER APP(S) 148
END

SYSTEMS, APPARATUSES AND METHODS FOR CAPTURING IMAGES OF MEDICAL CONDITION MANAGEMENT EVENTS

REFERENCE TO RELATED APPLICATION

This application claims the benefit of U.S. provisional patent application Ser. No. 63/017,347, filed Apr. 29, 2020; the entire contents of which are hereby incorporated herein by reference.

BACKGROUND

1. Field

Apparatuses and methods consistent with example embodiments relate to drug delivery devices such as syringes, autoinjector pens, and wearable autoinjectors for transferring (i.e., injecting or withdrawing) fluids, and more particularly to a syringe and/or related components (e.g., syringe needle shields and needle guards), or an autoinjector pen, or wearable autoinjector provided with mutable indicia to provide information about status (e.g., use or stage of use) of a syringe or syringe component, or autoinjector, or fill volume, or delivered dose, among other information, and a smartphone application (app) that facilitates capture and transmission of the information.

2. Description of the Related Art

Medication non-adherence is an issue of global importance, particularly with regard to diabetes care. An estimated fifty percent of all patients do not take their medication as prescribed. Non-adherence directly contributes to hundreds of thousands of deaths and billions of dollars in avoidable medical and related costs.

Smartphone apps are currently in use, which use a picture of a prescription label to help a patient reorder when their supply of prescribed medication is low. However, these apps do not directly identify the medication or the dose prior to the patient taking the medication, and are not of particular use in conjunction with syringes or pen injectors.

There are other smartphone apps that assist users with recording medical events such as injections, and smart injection devices (i.e., smart pen injectors) that can assist users with automatically logging dialed amounts for delivery and/or delivered amounts of medication.

Nonetheless, there remains a continuing need for methods and devices to assist users (e.g., patients, their caregivers, their healthcare providers and other medical condition management stakeholders such as payers/insurance companies, pharmacies, and medical products suppliers and distributors) in the acquisition and use of information related to medical condition management events to track compliance with medical condition management protocol or regimen, improve related processes such as replenishment of medical supplies, prevent medical errors such as medication delivery errors, and facilitate information sharing among medical condition management stakeholders for optimal patient treatment plan of care, billing, and insurance coverage purposes.

Effective administration of some types of drug injections, particularly in the case of insulin used by diabetics, requires that a record be kept of all administered doses. Many patients use low cost, and often disposable, delivery devices such as syringes or autoinjector pens to deliver their prescribed medication. Although these devices are relatively simple to use, these drug delivery devices typically lack any features to help patients or health care personnel record their use in connection with compliance with a medication treatment regimen.

For example, patients are encouraged to record date and time and amount of a self-injection via a syringe or autoinjector pen. While education is offered for self-injection patients, most patients still find it challenging to follow the instructions properly on a daily basis. Additionally, the only means for obtaining a record of injections and dosages injected is by writing it down manually. Also, certain patients may find it difficult to draw a very specific amount of a drug into a syringe and/or determine a specific amount of a drug that has been injected due to a difficulty in reading scale markings on the barrel of the syringe or in appropriately following instructions.

Difficulties with recording injection information via syringes and autoinjector pens can also be present in clinical settings. For example, although health care personnel can be better trained than patients to record dose-related information, there is significant overhead associated with capturing this information. It can be difficult in terms of time and convenience for health care personnel to measure and record certain injection times and dosages in a clinical setting with multiple patients.

SUMMARY

Example embodiments may address at least the above problems and/or disadvantages and other disadvantages not described above. Also, example embodiments are not required to overcome the disadvantages described above, and may not overcome any of the problems described above.

A need exists for an improved drug delivery device that can provide a user with more convenient, more consistent and more accurate capture of information regarding injection events and delivered doses for improved adherence to a prescribed medication dosage regimen.

In accordance with an example embodiment, a medical delivery system comprises a drug delivery device selected from the group comprising a syringe, an autoinjector pen, and a wearable autoinjector. The drug delivery device has a mutable indicia that is altered after a designated operation of the drug selected from the group consisting of removal of a pen cap or needle cap, movement of a plunger or other drive mechanism to dispense a fluid from the drug delivery device, mechanical motion of a component of the drug delivery device, and movement of a drug delivery device component after the fluid is dispensed. The medical delivery system also comprises a set of computer-readable instructions that analyze an image of the mutable indicia and assign a first state of the drug delivery device when analysis of the image detects that the mutable indicia is unaltered, and assign a second state of the drug delivery device when analysis of the image detects that the mutable indicia has been altered by the designated operation of the drug delivery device, and stores the assigned states in a memory device.

According to an aspect of an example embodiment, the set of computer-readable instructions associates and stores in the memory device respective time stamps corresponding to the assigned states.

According to an aspect of an example embodiment, the set of computer-readable instructions is in a software application stored in a memory of a digital device, and the image is generated by a camera associated with the digital device.

According to an aspect of an example embodiment, the first indicia comprises one or more characteristics selected from the group consisting of a machine-readable code, a barcode, printed indicia, etched indicia, alphanumeric indicia, color-coded indicia, optical indicia, indicia representing a measurement scale, indicia comprising one or more stripes, and indicia comprising one or more shapes.

According to an aspect of an example embodiment, the first indicia is altered by an operation selected from extending the first indicia, shortening the first indicia, changing an optical property of the first indicia, and changing a physical property of the first indicia.

According to an aspect of an example embodiment, wherein the set of computer-readable instructions are configured to communicate the determined first state or second state to another device.

According to an aspect of an example embodiment, the drug delivery device is a syringe and the mutable indicia comprises at least a first indicia provided on the syringe. The syringe comprises a barrel having a cavity for holding a fluid, an opening at a proximal end thereof for receiving a plunger, an opening at a distal end thereof in fluid connection with a needle, and a plunger movable within the cavity of the barrel and comprising a stopper on a distal end thereof. The set of computer-readable instructions analyzes an image of the first indicia and assigns the first state to the syringe when analysis of the image detects that the first indicia is unaltered, and assigns the second state to the syringe when analysis of the image detects that the first indicia has been altered by the movement of the plunger.

According to an aspect of an example embodiment, the set of computer-readable instructions are configured to communicate the determined state of the syringe to another device.

According to an aspect of an example embodiment, the first state of the syringe is a pre-delivery state, and the second state of the syringe is selected from the group consisting of delivery commenced by movement of plunger, and delivery completed by movement of plunger to an end position.

According to an aspect of an example embodiment, the set of computer-readable instructions is configured to determine a state of the syringe selected from the group consisting of a movement distance of the plunger, an amount of fluid remaining in the syringe, and an amount of fluid delivered from the syringe by movement of the plunger.

According to an aspect of an example embodiment, the mutable indicia can comprise a second indicia, and the plunger is provided with at least one of a stopper and the second indicia on the plunger or the stopper. Analysis of the image detects that the first indicia is altered by the movement of the plunger when a condition occurs that is selected from the first indicia being at least partially obscured by the stopper, the first indicia being at least partially obscured by the second indicia, and the first indicia and second indicia being combined in the image to represent the second state of the syringe.

According to an aspect of an example embodiment, the syringe comprises a needle shield removably affixed to the syringe, the needle shield being configured to cover the needle before the needle shield is removed and to expose the needle after the needle shield is removed. The first indicia is provided on the needle shield and configured to be altered by removal of the needle shield from the syringe. The first state of the syringe is the needle shield affixed to the syringe, and the second state of the syringe is the needle shield removed from the syringe.

According to an aspect of an example embodiment, the set of computer-readable instructions are configured to communicate, to another device, the determined first state of the needle shield affixed to the syringe, or the determined second state to the needle shield removed from the syringe.

According to an aspect of an example embodiment, the first indicia is provided on the syringe as a printed label affixed to the syringe and operable for a portion of the printed label to be torn away from the syringe upon removal of the needle shield from the syringe and thereby altering the first indicia.

According to an aspect of an example embodiment, the needle obscures at least part of the first indicia when the needle shield is affixed to the syringe to represent the first state of the syringe, and the first indicia is not obscured by the needle when the needle shield is removed from the syringe to represent the second state of the syringe.

According to another aspect of an example embodiment, medical delivery system further comprised a needle guard. The needle guard has a needle guard plunger having a plunger cavity to at least partially receive the syringe, and a body having a body cavity to at least partially receive the needle guard plunger. The needle guard plunger has an opening at its proximal end to receive the syringe into the plunger cavity and an opening at its distal end through which the needle of the syringe extends when in a pre-delivery state. The body has a spring mechanism at its distal end that engages the distal end of the needle guard plunger in an energy storage state during the pre-delivery state. The spring mechanism is operable in a released energy state to advance the needle guard plunger and the syringe toward a proximal end of the body to retract the needle of the syringe into the body after the syringe has completed a delivery of fluid therefrom. The first indicia provided on the syringe is unaltered during the pre-delivery state and is altered after the spring mechanism advances the needle guard plunger and the syringe to retract the needle into the body.

According to an aspect of an example embodiment, the body comprises a window through which the first indicia on the syringe is viewable.

According to an aspect of an example embodiment, the mutable indicia can comprise a second indicia, and the plunger of the syringe is provided with at least one of a stopper and the second indicia on the plunger or the stopper. Analysis of the image detects that the first indicia is altered by the movement of the plunger when a condition occurs that is selected from the first indicia being at least partially obscured by the stopper, the first indicia being at least partially obscured by the second indicia, and the first indicia and the second indicia being combined in the image to represent the second state of the syringe.

According to an aspect of an example embodiment, analysis of the image employs a combination of the first indicia and the second indicia to detect that the spring mechanism has advanced the needle guard plunger and the syringe to retract the needle into the body.

According to an aspect of an example embodiment, the mutable indicia can comprise a second indicia, and the plunger of the syringe is provided with the second indicia, analysis of the image employs a combination of the first indicia and the second indicia to detect that the spring mechanism has advanced the needle guard plunger and the syringe to retract the needle into the body.

According to an aspect of an example embodiment, analysis of the image comprises determining whether the combination of the first indicia and the second indicia comprises an altered indicia with increased length than the first indicia or the second indicia.

According to an aspect of an example embodiment, the set of computer-readable instructions are configured to communicate, to another device, the determined first state corresponding to the syringe being unaltered during the pre-delivery state, or the determined second state corresponding to advancement of the needle guard plunger and the syringe to retract the needle into the body.

According to an aspect of an example embodiment, a needle guard comprises a needle guard plunger having a plunger cavity to at least partially receive a syringe, and a body having a body cavity to at least partially receive the needle guard plunger. The needle guard plunger has an opening at its proximal end to receive the syringe into the plunger cavity and an opening at its distal end through which a needle of the syringe extends when in a pre-delivery state. The body has a spring mechanism at its distal end that engages the distal end of the needle guard plunger in an energy storage state during the pre-delivery state, the spring mechanism is operable in a released energy state to advance the needle guard plunger and the syringe toward a proximal end of the body to retract the needle of the syringe into the body after the syringe has completed a delivery of fluid therefrom. The mutable indicia comprises a first indicia provided on the body and a second indicia provided on the needle guard plunger, the mutable indicia being assigned by the set of instructions to the first state during the pre-delivery state and being assigned to the second state when it is altered after the spring mechanism advances the needle guard plunger and the syringe to retract the needle into the body.

According to an aspect of another example embodiment, the drug delivery device is an autoinjector pen and the mutable indicia is provided on at least one of a pen cap removably affixed to the autoinjector pen, a needle removably affixed to the autoinjector pen, a dose window through which a fluid for delivery and a drive mechanism configured to expel the fluid from the autoinjector pen are visible, and a fluid cartridge if the autoinjector pen is reusable. According to an aspect of another example embodiment, the mutable indicia is provided on the dose window or on the body of the autoinjector pen and adjacent to the dose window, and the drive mechanism has a rubber seal at its distal end that is translated to dispense the fluid. The set of computer-readable instructions analyzes one or more images of the mutable indicia, and assigns the first state to the drug delivery device when analysis of the one or more images detects that the mutable indicia is unaltered, and assigns the second state to the drug delivery device when analysis of the one or more images detects a condition selected from the group consisting of the mutable indicia being at least partially obscured by the rubber seal, a change in the location of an obscured part of the mutable indicia by the rubber seal, and a change in the mutable indicia relative to a measurement scale provided on the dose window or on the body adjacent resulting from at least one of fluid dispensing or rubber seal movement.

BRIEF DESCRIPTION OF THE DRAWINGS

The above and/or other example aspects and advantages will become apparent and more readily appreciated from the following description of example embodiments, taken in conjunction with the accompanying drawings in which:

FIG. 1 illustrates an example syringe according to the related art;

FIGS. 2A, 2B illustrate an example needle according to the related art.

FIG. 8 is a flow chart of example operations of syringe with mutable indicia and external device, according to an illustrative embodiment.

DETAILED DESCRIPTION OF EXAMPLE EMBODIMENTS

Figures 2C, 2D:
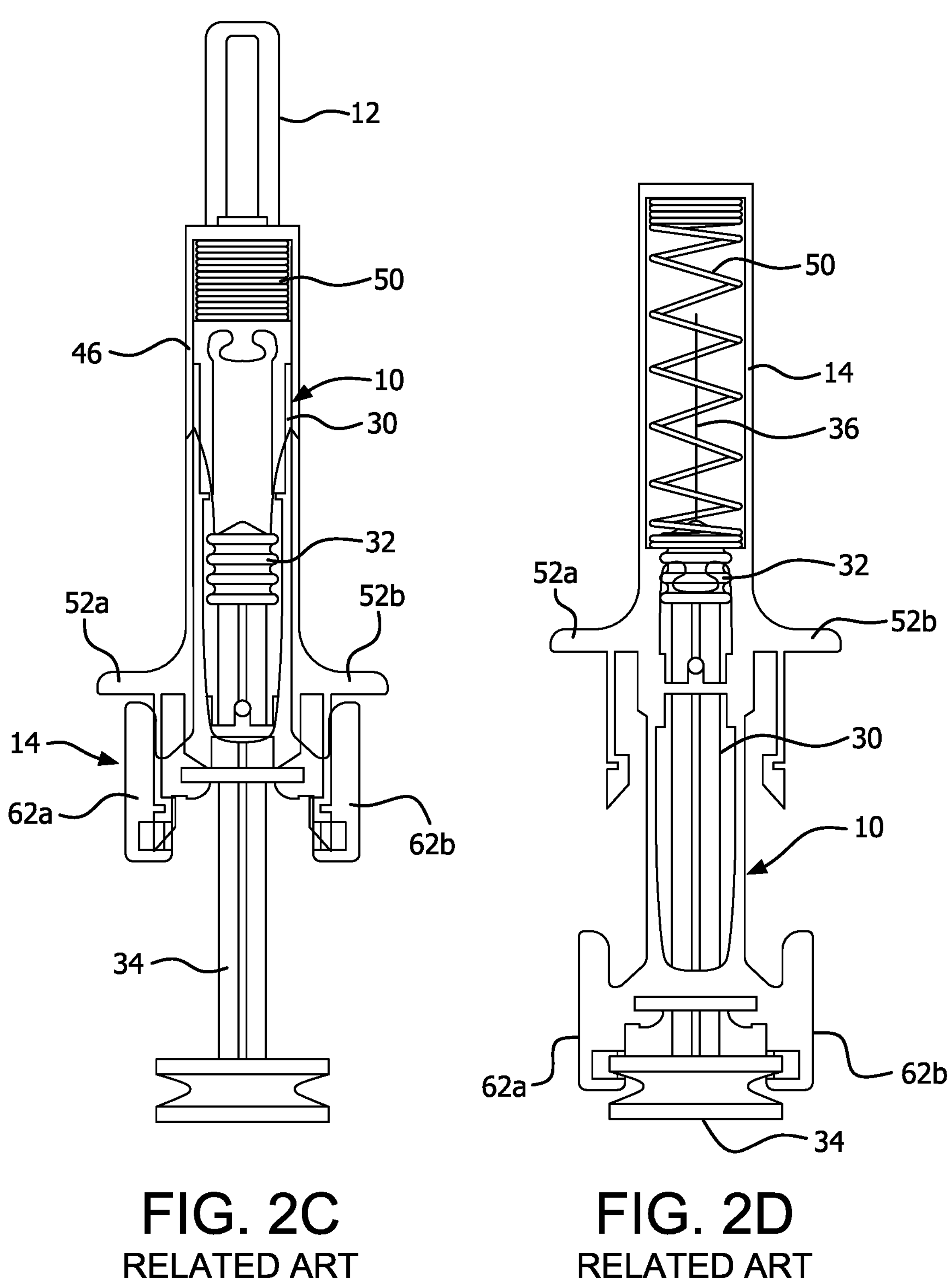
FIGS. 2C and 2D illustrate the needle guard of FIGS. 2A, 2B but with an example syringe deployed therein.

Reference will now be made in detail to example embodiments which are illustrated in the accompanying drawings, wherein like reference numerals refer to like elements throughout. In this regard, the example embodiments may have different forms and may not be construed as being limited to the descriptions set forth herein.

Example embodiments described herein provide low cost solutions for adding smart features to drug delivery devices such as syringes, or autoinjectors (e.g., autoinjector pens or wearable) often used in the self-administered injection business. Example embodiments described herein employ indicia on a drug delivery device whereby the indicia is mutable; that is, the indicia is physically altered, or a captured image or scan of the indicia is altered, depending a change in the state of the drug delivery device.

Examples of indicia include, but are not limited to, barcodes or other markers or patterns that can be scanned or otherwise recognized by different technologies in several ways. The indicia can be, for example, a pattern such as a barcode, or alphanumeric indicia (e.g., a measurement scale indicating units of measurement), or color-coded indicia, or indicia comprising one or more shapes. The indicia can be implemented as a temperature sensitive barcode that, when applied relative to a fluid chamber of a drug delivery device, can facilitate determining the temperature of the fluid as well as providing information represented by the barcode. The indicia can be printed directly on the drug delivery device or on a label applied to a drug delivery device or related component, or etched into a material of the delivery device or related component.

In accordance with an aspect of example embodiments, the indicia on the drug delivery device is mutable, that is, altered depending on a change in state of operation or use of the drug delivery device. For example, the indicia can be altered by a change in a barcode or pattern from obfuscation of a portion thereof by a part or component of the drug delivery device, or a change in color during use of the drug delivery device, or a change in transparency (e.g., a change in state of drug delivery device causes the indicia and/or material employed on a drug delivery device to become scratched or otherwise less transparent).

Examples of indicia scanners or readers are a smartphone or an even lower cost dedicated barcode scanner, or other optical detection device such as a photometer for determining change in color or transparency of a material used as an indicator of drug delivery device state change. An indicia reader can also be an image capture and processing device. Examples described herein use a camera on a smartphone or iPad or other smart device. For example, scanning a changed barcode on a syringe or pen injector or wearable autoinjector that is changed after use (e.g., after an injection) can help a patient track injection information in a convenient app (e.g., amount of dose, date/time if dose, etc.) as described further below. The app can be a mobile phone app or otherwise a set of computer-readable instructions in a software application provided on a smart device such as a smart display device (e.g., Google Nest Hub) or similar device.

For example, in accordance with an illustrative embodiment, a mobile phone with integrated digital camera can be provided with a software application (i.e., mobile phone app) that receives a camera image of indicia on a drug delivery device taken in connection with a stage of device use (e.g., indicia altered by removal of a needle cap or pen cap, or altered after an injection), and analyzes the indicia captured in the image to automatically determine and record in memory information about the drug delivery device represented by the indicia. For example, the indicia can include predetermined information such as drug type, or expiry date, or pen needle type represented in a barcode, as well as the mutable indicia of the example embodiments, or the indicia can comprise only mutable indicia. The app can be programmed to recognize unaltered and altered forms of the mutable indicia captured in an image and associate designated states or other meanings with the captured mutable indicia. A image of unaltered mutable indicia can be associated by the app with a pre-delivery state of the drug delivery device, whereas an image of the indicia indicating alteration thereof (e.g., partially obscured by a drug delivery device component or extended by another combined code on a drug delivery device component, or change in transparency or color) can be associated by the app with different state of the drug delivery device such as a partial-delivery or post-delivery state, or a deployment of a safety feature after injection. The app can record these detected states along with a date and/or timestamp automatically in a memory device, thereby facilitating a user's capture of medical event information related to their injections. A user need only take a photograph of their drug delivery device during an injection, and the mobile phone processor and app will analyze the indicia in the capture image and determine and record the drug delivery device state.

Some example embodiments of mutable indicia on a drug delivery device include, but are not limited to:

1. A syringe is provided with indicia (e.g., a barcode other pattern) that has lines or other marks interspaced with the transparent material of the syringe barrel, for example. As a syringe stopper or other mechanical part of the injector moves behind the barcode, it obscures certain portions of the barcode or pattern, thereby changing the value or meaning of that barcode or pattern read by a reader or scanner or phone app.
2. A barcode or other pattern is covered or uncovered as part of the injector's mechanism. For example, if a barcode is provided on underneath a movable part of a pre-filled safety syringe, the barcode would be revealed after the deployment of the safety shield. Such mutable indicia provided on a safety feature facilitates tracking of device types and whether safety features successfully deployed after injections. Such information can be useful in a clinical setting for context-based training, staff procedures compliance tracking, and supply replenishment.
3. A temperature sensing barcode is added to a self-injection device to sense drug temperature, which can be a useful parameter.
4. A combination of any two or all of the above embodiments of mutable indicia can be provided to a drug delivery device to facilitate recording of injection event information such as which devices were used, date and time of injection, status of fluid (e.g., temperature) and whether safety features successfully deployed.

In accordance with example embodiments, a medical event image capture app 114 (FIG. 7) is described herein that can be a standalone app on a smartphone 20 or other portable device with camera (e.g., an iPad), or can be provided as an enhancement to a digital health (DH) app for a smartphone or other smart, connected device. The medical event image capture app 114 uses image(s) of mutable indicia on a drug delivery device to automate analysis and determination of the imaged state of the drug delivery device and recording of related information in a memory device (e.g., pre-delivery or post-delivery state along with date or time of image capture, delivered dose or remaining amount, deployment of safety feature, among other states of operation). The additional informatics from the captured medical product images can be used by different functions of the app to assist with various aspects of medical condition management such as training, compliance tracking, accuracy of dose amounts, supply replenishment, among others.

Figure 7:
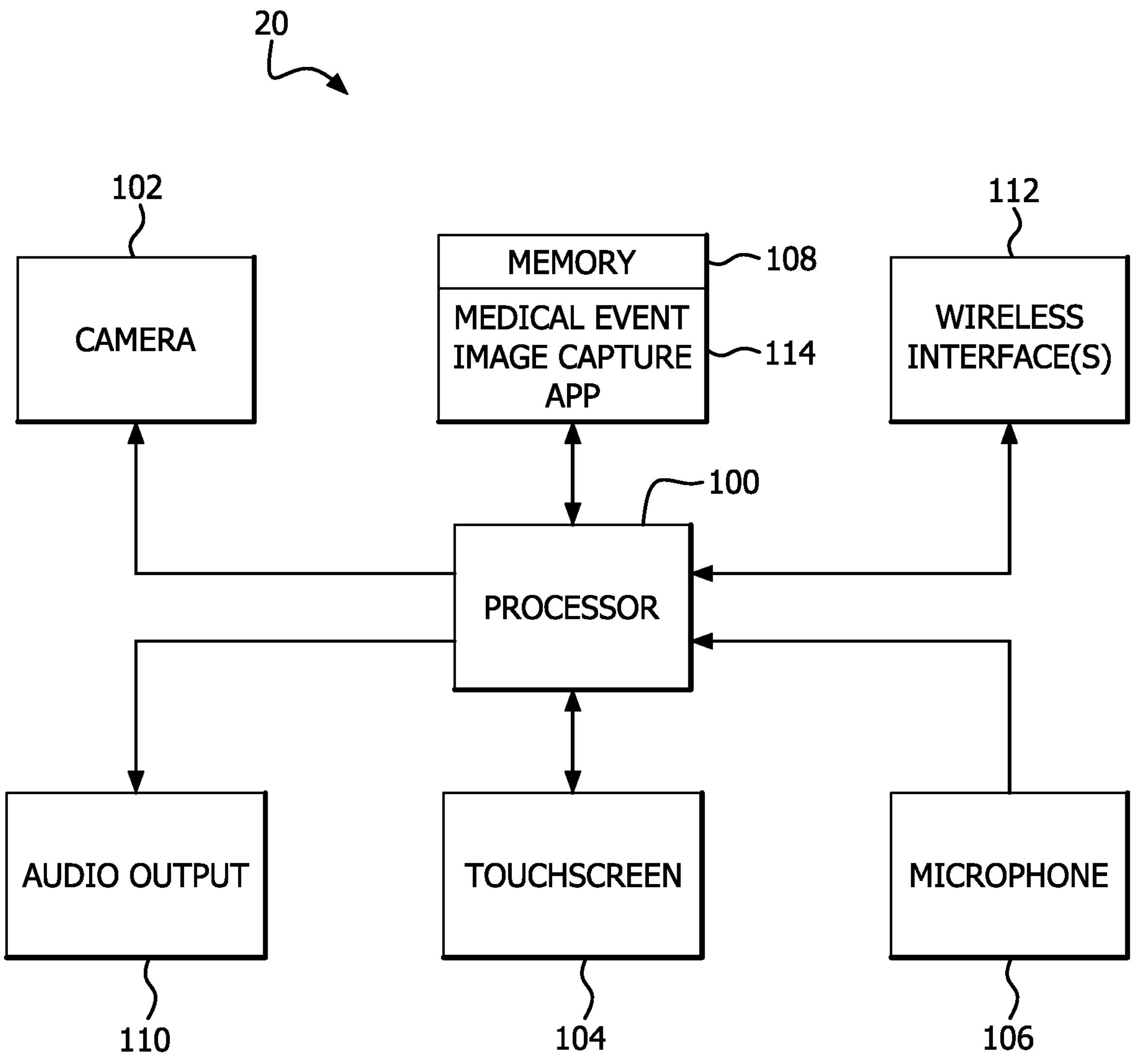
FIG. 7 illustrates a block diagram of an example mobile phone with medical event image capture application, according to an illustrative embodiment.

FIG. 7 is a block diagram depicting an example device 20. The device 20 is referred to as a smartphone, but it is understood that the device 20 can be a dedicated medical management device or other portable, handheld device (e.g., iPad) with an indicia image capture or reader device 102 such as a camera. The device 20 comprises a processor 100, and a memory 108 that can store a medical event image capture app 114 in accordance with an illustrative embodiment, along with other device data, images and apps. The device 20 can have one or more wireless communication interface(s) 112 such as a near field communication (NFC) interface, a Bluetooth®-enabled wireless communications interface, and/or a cellular communications interface, for example. The device 20 can also have different user interfaces such as one or more of a microphone 106, touchscreen 104 or other display device that generates graphical user interface (GUI) screens such as those of the medical event image capture app 114, optional keypad or other user input device (not shown), and an audio signal output device (e.g., speaker or buzzer) 110.

The medical event image capture app 114 is program code that provides indicia and/or drug delivery device image capture operations, and captured image processing operations. The captured image processing operations can (1) decode or otherwise discern artifacts and related informatics from indicia and other image elements in the captured image, (2) conveniently automatically record data related to a medical event such as needle cover removal prior to dosing, dosing or otherwise moving the plunger, medical fluid level in a syringe, and needle guard activation after dosing where applicable, and (3) perform human machine interaction (HMI) operations or other logical operations that alert a user regarding a selected infomatic and request input or otherwise educate the user about a related medical event.

For example, the image capture operation captures images from the device camera 102. The captured image processing operations can implement a two-dimensional (2D) image and/or or three-dimensional (3D) image processing algorithm to detect selected artifacts from the captured image(s). The captured image processing operations can optionally include a recognition operation such as a QR code reader, barcode or UPC code reader, or optical character recognition (OCR) operation within the app 114. The HMI or other operations of the medical event image capture app 114 determine from the detected artifacts (e.g., the mutable indicia and other aspects of the imaged drug delivery device) what state the imaged drug delivery device is in and record related infomatics in a digital memory device.

Many patients use low cost, and often disposable, delivery devices such as syringes or autoinjector pens or wearable autoinjectors (e.g., Libertas™ available from Becton, Dickinson and Company) to deliver their prescribed medication. As shown in FIG. 1, a typical syringe 10 is made primarily of plastic or glass and has several components including a barrel 30, a stopper 32, a plunger 34, and a needle 36. Scale printing can be provided on the barrel to enable proper dosing. Inside the barrel 30, the rubber stopper 32 creates a hermetic seal and displaces liquid medication or other fluid into and out of the barrel. The plunger 34 interfaces with the rubber stopper 32 to move it back and forth under the user's control. A metal needle 36 or cannula is usually attached to the distal end of the barrel to allow fluids to be injected into or removed from the body, although this is not always the case. For example, a syringe having a male Luer connector at its distal end can be attached to a female Luer connector on a catheter or IV line to inject or withdraw fluids without the use of a needle or cannula. Large numbers of syringes may be used in a relatively short period of time in hospital and care settings, and for management, by patients, of certain conditions. A needle may be detachably connected to a barrel using Luer-Lok™ or Luer slip connections 40, or it may be permanently attached or "staked" to the barrels during manufacture of the syringes.

A syringe 10 can often be used with one or more components such as a needle shield 12 or a needle guard 14. An example needle shield 12 is shown in FIG. 3 and is generally removed prior to injection.

FIGS. 2A, 2B, 2C and 2D show a typical needle guard 14 for a syringe 10 that is designed to retract the syringe following drug delivery to cover the syringe needle within a cavity 56 of the needle guard 14. The needle guard 14 comprises a body 46 with cavity dimensioned to receive a guard body plunger 54 that in turn has a cavity 56 dimensioned to receive a prefilled syringe 10. The plunger 54 is slidable within the body 46 cavity. The body 46 has a body inspection window 48 to see the plunger and syringe therein, a spring 50 at its distal end, and flanges 52 *a,b* at its proximal end to accommodate a user's fingers. The guard body plunger 54 has an opening 58 at its proximal end to receive the distal end of a syringe 10 and an opening 60 at its distal end through which the syringe needle with shield protrudes. The distal end circumference of the guard body plunger 54 abuts the spring 50. The guard body plunger 54 also has prongs 62*a,b* at its proximal end that form a recess to receive the proximal end of syringe plunger 34 when deployed.

Reference will now be made to FIGS. 3, 4A, 4B, 5 and 6, which illustrate example embodiments of an improved syringe 10, needle shield 12 and needle guard 14 that each employ mutable indicia and therefore provide a low cost solution to a technical problem of making logging of injection event data involving relatively low cost drug delivery devices more convenient to the user and to allow for collection of other relevant data related to an injection event. For example, the mutable indicia are provided directly on or applied as labels to the syringe 10 and/or to related components such as a needle shield 12 or needle guard 14 and are a relatively lower cost solution than other methods for collecting injection information such as providing syringes and autoinjectors with RFID tags or sensors or processors and communication interfaces.

Figure 3:
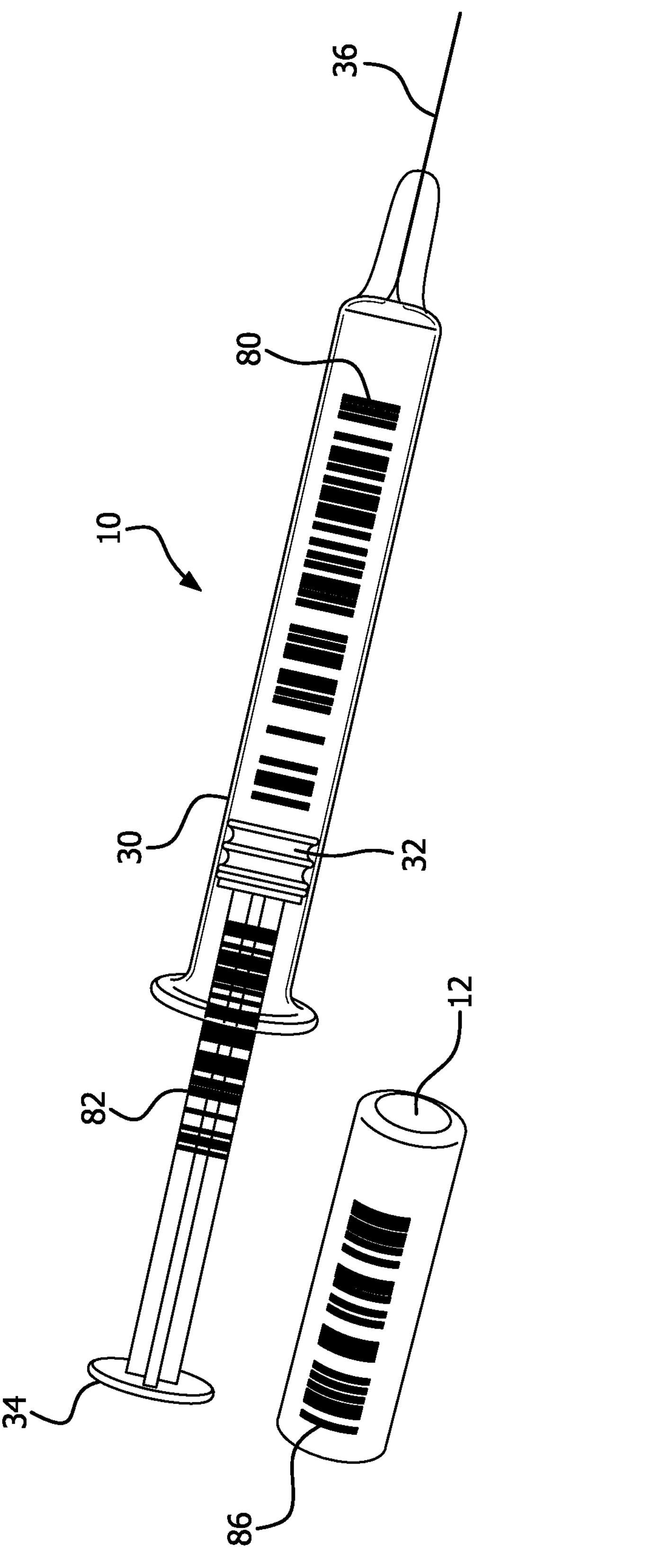
FIG. 3 illustrates an example syringe with mutable indicia, according to an illustrative embodiment.

FIG. 3 is an improved syringe 10 in accordance with an example embodiment that has mutable indicia 80 on its barrel 30. The indicia 80 is illustrated as a barcode but can be a different optical pattern, for example. The indicia 80 can represent a first state when it is unaltered (e.g. prior to drug delivery). When the plunger 34 is deployed, the plunger stopper 32 alters the indicia 80 as it appears to a reader or scanner by obfuscating at least part of the indicia 80. This alters the indicia 80 that can be assigned by the app 114 to represent a different state (e.g., a post delivery state, or a current dose state, or a fluid remaining state). Alternatively, the plunger 34 can be provided with a second indicia 82, and its combination with indicia 80, or its addition to the length of the indicia 80, or other means to alter the indicia 80 can represent a different assigned state. The second indicia 82 can be another barcode, for example, or other type of mark 84 on the plunger or stopper as shown in FIG. 5. The syringe 10 can optionally be used with an improved needle shield 12 that is provided with mutable indicia 86. The indicia 86 can be provided on a label from which a portion is torn away when the shield 12 is removed from the syringe 10 to alter the indicia 86 (e.g., make it shorter) and therefore represent a different state such as "injection event" versus a state of pre-injection event represented by unaltered indicia 86. Detection of alteration of the indicia 86 can result in storage of a time stamp corresponding to an "injection event." In other words, a user need only take a picture of the shield 12 removed from the syringe to automatically detect and record when an injection has occurred using the app 114. FIG. 5 illustrates a drug delivery device with mutable indicia having an image captured thereof using a camera 102 on a smartphone 20 with app 114. It is to be understood that the drug delivery devices shown in FIGS. 3, 4A, 4B and 6 can similarly be read by a smartphone camera 102 or other type of scanner.

Figures 4A, 4B:
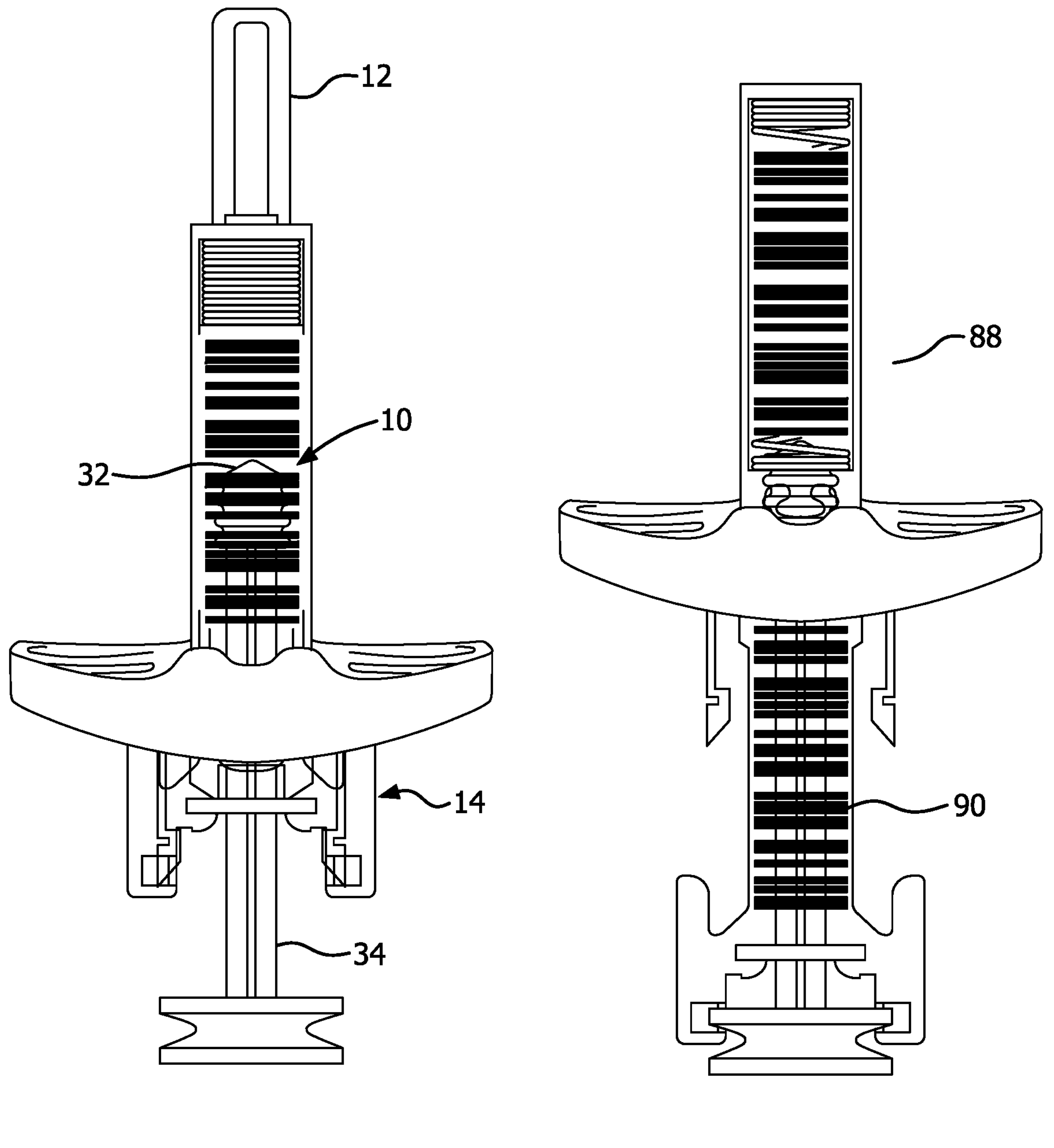
FIGS. 4A and 4B illustrate an example needle guard with syringe and mutable indicia, according to an illustrative embodiment.
Figure 5:
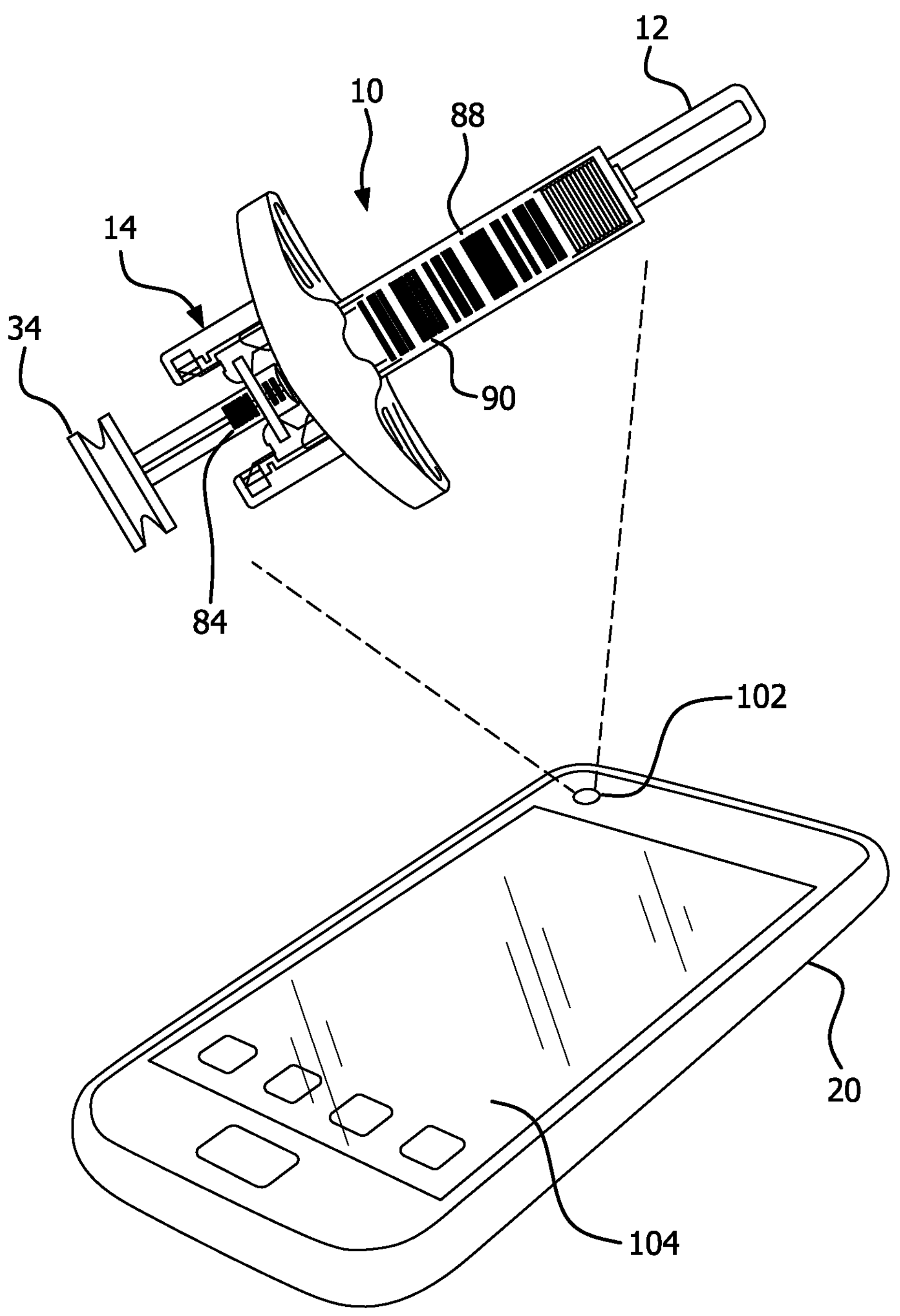
FIG. 5 illustrates an example image capture device generating an image of the needle guard with syringe in FIGS. 4A and 4B, according to an illustrative embodiment.

FIGS. 4A and 4B and 5 illustrate an improved syringe 10 with needle guard 14 having mutable indicia in accordance with example embodiments. The mutable indicia can comprise a first indicia 88 on the needle guard body 46 and a second indicia 90 on the needle guard plunger 54. The first indicia 88 is unaltered in FIG. 4A and can represent a pre-delivery state, and is altered (e.g., combined and lengthened) when deployed to retract the syringe needle into the needle guard body 46 and therefore represent a post-delivery state. Either state can be detected using a quick scan or image capture to log a time and state via the app 114, for example. Thus, the user is provided with another example convenient method of recording an injection event without having to manually write or type a date/time and other information.

Figure 6A:
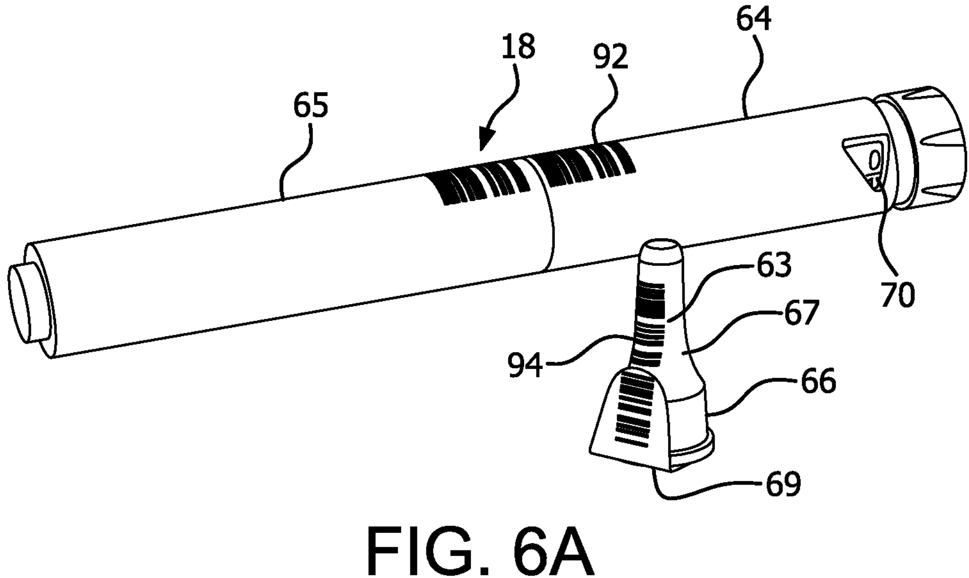
FIG. 6A illustrates an example autoinjector pen and/or pen needle adapter with mutable indicia, according to an illustrative embodiment.
Figure 6B:
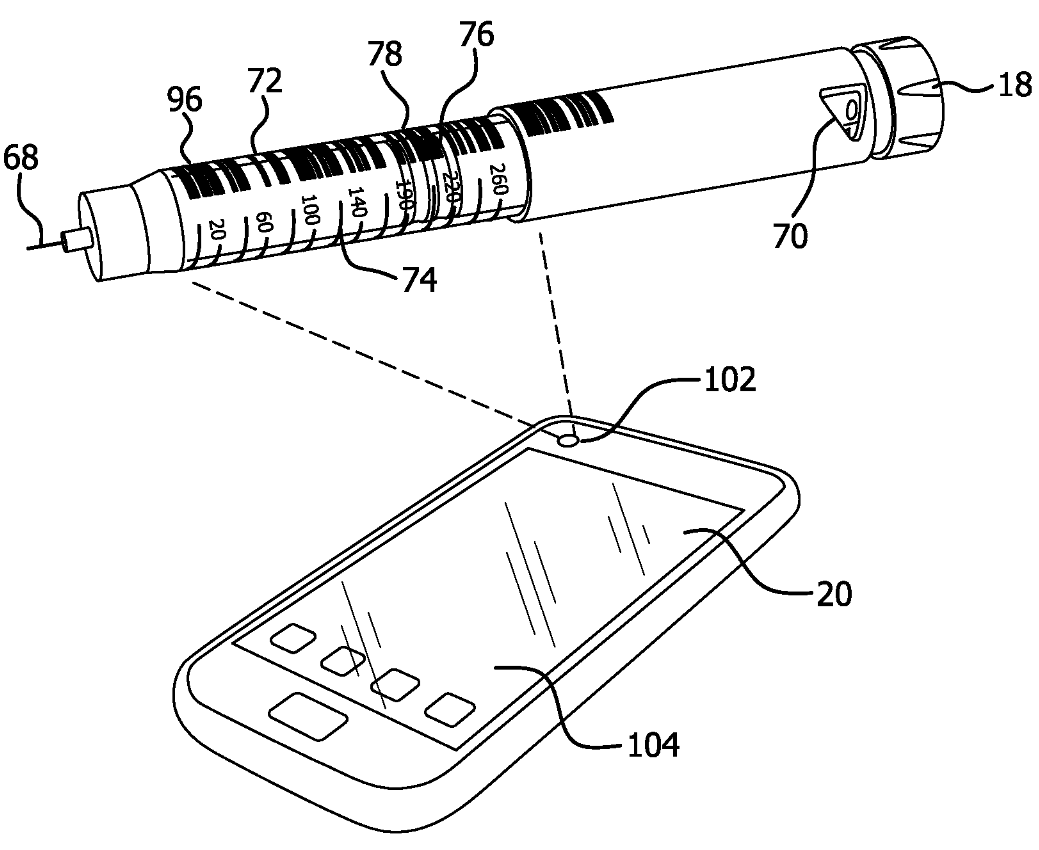
FIG. 6B illustrates an example autoinjector pen with mutable indicia, according to an illustrative embodiment.

The advantages of mutable codes is not limited to syringes and their related components, but can also be applied to autoinjector pens 18 and wearable autoinjectors. For example, many patients use relatively low cost disposable single-patient-use prefilled autoinjector pens to deliver a drug. For example, many diabetic patients use autoinjector pens that contain, for example, 300 units of insulin, allowing a patient to inject themselves with more than 1 dose from the pen 18. With reference to FIGS. 6A and 6B, an autoinjector pen 18 comprises a pen body 64 with cap 65 and dose dial and window 70. To inject, a user removes the cap 65 and connects a needle 68 to the pen 18. The pen 18 has a chamber 72 with fluid (e.g., prefilled, or with a fluid cartridge inserted therein) and a printed scale 74 to allow a user to visually discern the number units of fluid in the chamber 72. The pen 18 further comprises a drive mechanism 76 to controllably expel fluid from the chamber 72 through the needle 68 in accordance with the dose dial 70 setting.

The pen 18 is improved with low cost mutable indicia to allow a user to conveniently and inexpensively log injection events related to the pen 18. For example, the chamber 72 can be provided with mutable indicia 96 such as a barcode or other pattern. When the drive mechanism 76 is fully retracted, the mutable indicia 96 is unaltered and assigned by the app 114 to represent a pre-delivery state. After the pen 18 has been used for an injection, the stopper 78 on the drive mechanism 76 obscures at least a portion of the mutable indicia 96 to alter it and represent a different state. The processor 100 in accordance with the app 114 can analyze the mutable indicia 96 alone, or with physical characteristics of the chamber 72 (e.g., positon of stopper therein or relative to the scale 74), captured in a camera image, for example, to determine delivered dose and fluid remaining in the chamber 72 and to automatically record such information in digital memory.

Further, the needle 68 can be packaged as a needle adapter 66 comprising an outer cover 67 with a peel off label 69 that encloses the needle 68 with inner cover 63. With continued reference to FIGS. 6A and 6B, mutable indicia 92 can also be applied to the pen cap 65 and body 64 such that it is shortened when the pen cap is removed. Alternatively, mutable indicia 94 can be provided to the outer cover 67 and label 69 such that it is shortened when the label 69 is peeled off In either case, a user can take an image of the altered mutable indicia 92 or 94 prior to injection to conveniently record an injection event. Further, the mutable indicia 92 or 94 can also comprise barcode data indicating pen type and needle type which can also be recorded in digital memory.

Sets of instructions can implement subsets of the operations illustrated in FIG. 8. For example, steps 120-126 can be the primary operations of the instructions to capture an image of one or more mutable codes or other indicia on a drug delivery device, capture another image of the one or more mutable codes on the drug delivery device at a different time, and analyze the capture images to determine their respective stages of operation of the drug delivery device based on any detected changes in the mutable codes as between the images, and optionally provide each determined stage with a time and/or date stamp. Other example operations are illustrated in FIG. 8 to show example stages detected for an example syringe 10 used alone or with one or both of a needle shield 12 and a needle guard 14 and related example infomatics that can be generated from the images of the mutable indicia on one or more the syringe 10, needle shield 12, and needle guard 14.

FIG. 8 illustrates example operations of a smartphone 20 or other device (e.g., a dedicated scanning device or iPad) operated in accordance with a medical event image capture app 114. It is to be understood that example embodiments can comprise computer-readable instructions to implement subsets of the operations illustrated in FIG. 8. For example, steps 120-126 can be the primary operations of the instructions to capture an image of a drug delivery device with one or more mutable codes or other indicia (blocks 120 and 124), to analyze the captured image to identify the indicia and optional related attributes (block 122), and to process the indicia and optional related attributes to determine designated infomatics or content such as associating detected altered indicia with an assigned state of the drug delivery device (block 126). Other example operations 128-148 illustrated in FIG. 8 show example stages detected for an example syringe 10 used alone or with one or both of a needle shield 12 and a needle guard 14 and related example infomatics that can be generated from the images of the mutable indicia on one or more the syringe 10, needle shield 12, and needle guard 14. It is to be understood that the instructions can control other operations with regard to detecting one or more states of an autoinjector pen.

For example, for block 126, the computer-readable instructions in the app 114 can be configured to store information assigning different drug delivery device states or operations to corresponding ones of unaltered mutable indicia and one or more respective degrees of altered mutable indicia such as a pre-delivery state assigned to unaltered mutable indicia and a post-delivery state assigned to indicia captured in an image and having any obfuscation of its pattern. As another example, the app 114 can be configured to assign a first drug delivery device state to unaltered mutable indicia and a second drug delivery device state to an altered form of the mutable indicia whereby the indicia has been lengthened (combined with other indicia) or truncated, or has changed color or transparency. The app 114 can also be configured to process captured images of a syringe barrel or window in an autoinjector pen or wearable autoinjector and adjacent mutable indicia and determine an amount of fluid remaining, or a currently dialed dose or drawn amount in a syringe, or a delivered dose.

Figure 9A:
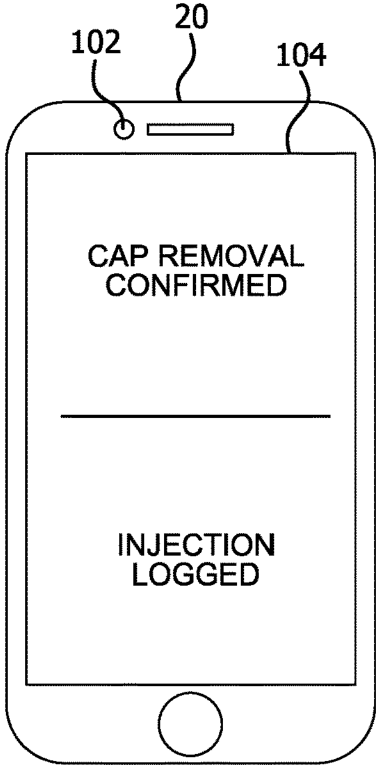
FIGS. 9A, 9B, 9C and 9D illustrate information which an app may cause to display on an external device, according to example embodiments.

With continued reference to example operations 128-148 in FIG. 8, a user operates a smartphone camera 102, or other device with a camera and the app 114, to take an image of a drug delivery device with mutable indicia at a selected point or stage of an injection event such as after removal of a pen cap or needle cap, or just before delivery, or just after plunger displacement, or after safety feature deployment (block 120). The app 114's captured image processing operation analyzes indicia and optionally other attributes of the drug delivery device (blocks 122 and 124). The app 114 is configured to control the processor 100 to determine the state of the drug delivery device and optionally other related device information (block 126). For example, the processor 100 in accordance with the app 114 can determine if a syringe needle shield 12 has been removed (block 128) indicating the beginning of an injection event and log a corresponding timestamp therefor (block 130 and FIG. 9A) based on indicia on the shield being altered or mutated by shield removal as described in connection with FIG. 3. Similarly, the processor 100 can determine if a syringe plunger or autoinjector drive mechanism has been moved (block 132) and log a corresponding timestamp therefore (block 134) based on indicia on the syringe barrel or autoinjector window being altered or obfuscated by the plunger stopper or the autoinjector drive mechanism, respectively, as described in connection with FIGS. 3, 4A, 4B, 5, 6A and 6B.

Figure 9B:
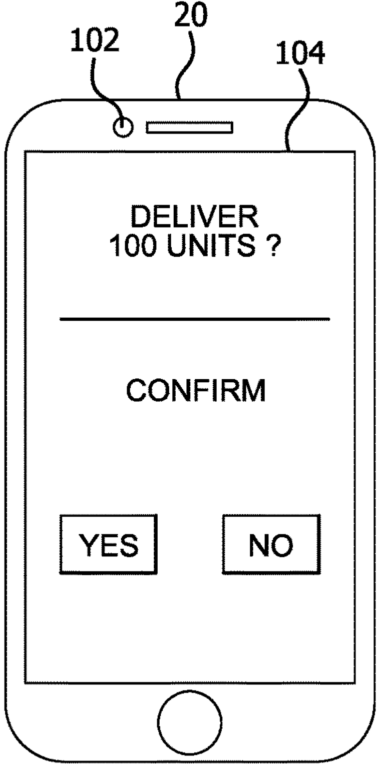
Figure 9C:
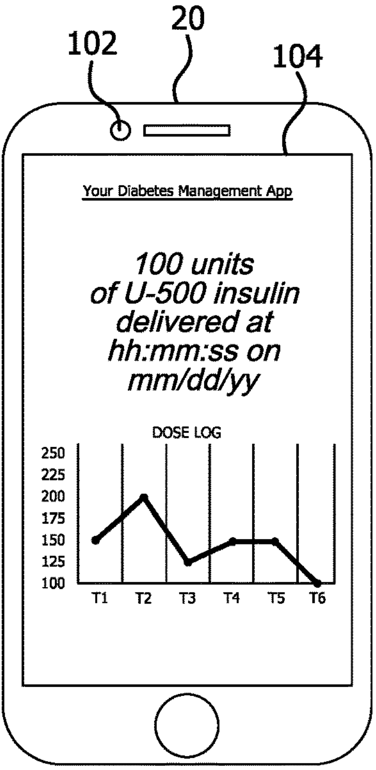
Figure 9D:
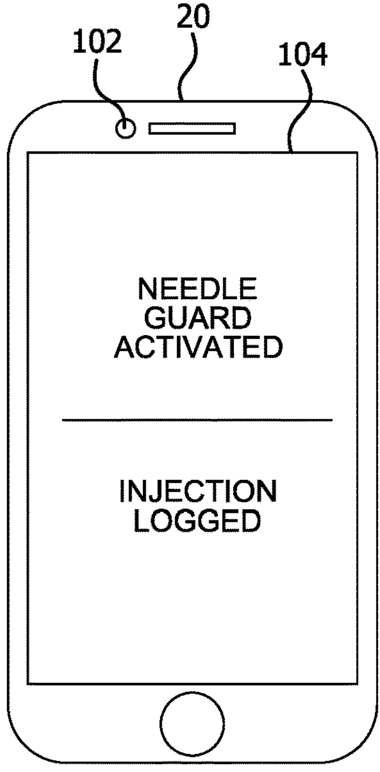

With continued reference to FIG. 8, the processor 100 is controlled by the medical event image capture app 114 to determine if the correct dose amount has been drawn or delivered and, if not, to optionally generate alerts or GUI screens to the user (blocks 136 and 138 and FIG. 9B). If a needle guard is used, the processor 100 can detect if this safety feature has deployed properly following an injection using first and second indicia for example, as described in connection with FIGS. 4A and 4B, and can optionally generate alerts or GUI screens to advise the user of any problem or failure (blocks 140 and 142 and FIG. 9D). The delivered dose can optionally be confirmed as delivered (e.g., via a GUI screen generated by the app 114 on the touchscreen 104) per block 144 and FIG. 9C. The medical event data or informatics (e.g., one or more of confirmed dose, detected malfunction, drug delivery states of operation, among other data obtained via the captured image processing operation of the app 114) can be stored locally or remotely for access and use by the patient and/or other medical condition management stakeholders (block 146). For example, the medical event data or informatics can be automatically uploaded to a repository for inclusion in a patient's electronic record, for medical billing, for auto-replenishment of medical supplies, and/or care plan compliance tracking, among other uses such as incorporation into an integrated disease management system (block 148).

Illustrative embodiments disclose multiple ways of better engaging with the user and leveraging the strengths from both drug delivery devices and the medical event image capture app 114 to enhance user experience. The app 114 is used to both identify specific features and activities, confirm they are as intended, provide confirmation to the user and also enable logging and tracking of information for posterity. Overall, the integrated usage of the drug delivery devices with mutable indicia and the app 114 can drive better compliance and improved patient outcomes. For example, illustrative embodiments described herein make logging of injection events and related information such as delivered dose more convenient, which can in turn provide more accurate data to enable better clinical decision making. While primarily geared towards a self-injecting patient base, the combination of the app 114 with drug delivery devices having mutable indicia can be leveraged in other settings (e.g., institutional and alternate sites) and also by caregivers (e.g., nurses, family members, etc.).

It will be understood that the terms "include," "including," "comprise," and/or "comprising," when used in this specification, specify the presence of stated features, integers, steps, operations, elements, and/or components, but do not preclude the presence or addition of one or more other features, integers, steps, operations, elements, components, and/or groups thereof.

It will be further understood that, although the terms "first," "second," "third," etc., may be used herein to describe various elements, components, regions, layers and/or sections, these elements, components, regions, layers and/or sections may not be limited by these terms. These terms are only used to distinguish one element, component, region, layer or section from another element, component, region, layer or section.

As used herein, the term "and/or" includes any and all combinations of one or more of the associated listed items. Expressions such as "at least one of," when preceding a list of elements, modify the entire list of elements and do not modify the individual elements of the list. In addition, the terms such as "unit," "-er (-or)," and "module" described in the specification refer to an element for performing at least one function or operation, and may be implemented in hardware, software, or the combination of hardware and software.

Various terms are used to refer to particular system components. Different companies may refer to a component by different names—this document does not intend to distinguish between components that differ in name but not function.

Matters of these example embodiments that are obvious to those of ordinary skill in the technical field to which these example embodiments pertain may not be described here in detail.

The components of the illustrative devices, systems and methods employed in accordance with the illustrated embodiments described herein can be implemented, at least in part, in digital electronic circuitry, analog electronic circuitry, or in computer hardware, firmware, software, or a combination thereof. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or other device or on multiple device at one site or distributed across multiple sites and interconnected by a communication network. Also, functional programs, codes, and code segments for accomplishing features described herein can be easily developed by programmers skilled in the art. Method steps associated with the example embodiments can be performed by one or more programmable processors executing a computer program, code or instructions to perform functions (e.g., by operating on input data and/or generating an output). Method steps can also be performed by, and apparatuses described herein can be implemented as, special purpose logic circuitry, e.g., a field programmable gate array (FPGA) or an application-specific integrated circuit (ASIC), for example.

The various illustrative logical blocks, modules, and circuits described in connection with the embodiments described herein may be implemented or performed with a general purpose processor, a digital signal processor (DSP), an ASIC, a FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., electrically programmable read-only memory (ROM) (EPROM), electrically erasable programmable ROM (EEPROM), flash memory devices, and data storage disks (e.g., magnetic disks, internal hard disks, or removable disks, magneto-optical disks, and CD-ROM and DVD-ROM disks). The processor and the memory can be supplemented by, or incorporated in special purpose logic circuitry.

Computer-readable non-transitory media includes all types of computer readable media, including magnetic storage media, optical storage media, flash media and solid state storage media. It should be understood that software can be installed in and sold with a central processing unit (CPU) device. Alternatively, the software can be obtained and loaded into the CPU device, including obtaining the software through physical medium or distribution system, including, for example, from a server owned by the software creator or from a server not owned but used by the software creator. The software can be stored on a server for distribution over the Internet, for example.

It may be understood that the example embodiments described herein may be considered in a descriptive sense only and not for purposes of limitation. Descriptions of features or aspects within each example embodiment may be considered as available for other similar features or aspects in other example embodiments. While exemplary embodiments have been described with reference to the figures, it will be understood by those of ordinary skill in the art that various changes in form and details may be made therein without departing from the spirit and scope as defined by the following claims.

What is claimed is:

1. A medical delivery system comprising:

a drug delivery device selected from the group comprising a syringe, an autoinjector pen, and a wearable autoinjector, the drug delivery device comprising a mutable indicia that is altered after a designated operation of the drug delivery device selected from the group consisting of removal of a pen cap or needle cap, movement of a plunger or other drive mechanism to dispense a fluid from the drug delivery device, mechanical motion of a component of the drug delivery device, and movement of a drug delivery device component after the fluid is dispensed; and a set of computer-readable instructions that analyze an image of the mutable indicia and assign a first state of the drug delivery device when analysis of the image detects that the mutable indicia is unaltered, and assign a second state of the drug delivery device when analysis of the image detects that the mutable indicia has been altered by the designated operation of the drug delivery device, and stores the assigned states in a memory device, wherein the syringe comprises a needle shield removably affixed to the syringe, the needle shield being configured to expose the needle after the needle shield is removed, the mutable indicia being configured to be altered by removal of the needle shield from the syringe, the first state of the syringe being the needle shield affixed to the syringe and the second state of the syringe being the needle shield removed from the syringe.

2. The medical delivery system of claim 1, wherein, the needle shield being configured to cover the needle before the needle shield is removed, and the mutable indicia being provided on the needle shield.

3. The medical delivery system of claim 2, wherein the set of computer-readable instructions are configured to communicate, to another device, the determined first state of the needle shield affixed to the syringe, or the determined second state to the needle shield removed from the syringe.

4. The medical delivery system of claim 2, wherein the mutable indicia is provided on the syringe as a printed label affixed to the syringe and operable for a portion of the printed label to be torn away from the syringe upon removal of the needle shield from the syringe and thereby altering the mutable indicia.

5. The medical delivery system of claim 2, wherein the needle obscures at least part of the mutable indicia when the needle shield is affixed to the syringe to represent the first state of the syringe and the mutable indicia is not obscured by the needle when the needle shield is removed from the syringe to represent the second state of the syringe.

6. A medical delivery system comprising:

a drug delivery device selected from the group comprising a syringe, an autoinjector pen, and a wearable autoinjector, the drug delivery device comprising a mutable indicia that is altered after a designated operation of the drug delivery device selected from the group consisting of removal of a pen cap or needle cap, movement of a plunger or other drive mechanism to dispense a fluid from the drug delivery device, mechanical motion of a component of the drug delivery device, and movement of a drug delivery device component after the fluid is dispensed; and a set of computer-readable instructions that analyze an image of the mutable indicia and assign a first state of the drug delivery device when analysis of the image detects that the mutable indicia is unaltered, and assign a second state of the drug delivery device when analysis of the image detects that the mutable indicia has been altered by the designated operation of the drug delivery device, and stores the assigned states in a memory device, wherein the drug delivery device is a syringe and the mutable indicia comprises at least a first indicia provided on the syringe, the syringe comprising a barrel having a cavity for holding a fluid, an opening at a proximal end thereof for receiving a plunger, an opening at a distal end thereof in fluid connection with a needle, and a plunger movable within the cavity of the barrel and comprising a stopper on a distal end thereof; and wherein the set of computer-readable instructions analyzes an image of the first indicia and assigns the first state to the syringe when analysis of the image detects that the first indicia is unaltered, and assigns the second state to the syringe when analysis of the image detects that the first indicia has been altered by the movement of the plunger, the medical delivery system further comprising a needle guard comprising a needle guard plunger having a plunger cavity to at least partially receive the syringe, and a body having a body cavity to at least partially receive the needle guard plunger, the needle guard plunger having an opening at its proximal end to receive the syringe into the plunger cavity and an opening at its distal end through which the needle of the syringe extends when in a pre-delivery state, the body having a spring mechanism at its distal end that engages the distal end of the needle guard plunger in an energy storage state during the pre-delivery state, the spring mechanism operable in a released energy state to advance the needle guard plunger and the syringe toward a proximal end of the body to retract the needle of the syringe into the body after the syringe has completed a delivery of fluid therefrom;

wherein the first indicia provided on the syringe is unaltered during the pre-delivery state and is altered after the spring mechanism advances the needle guard plunger and the syringe to retract the needle into the body.

7. The medical delivery system of claim 6, wherein the body comprises a window through which the first indicia on the syringe is viewable.

8. The medical delivery system of claim 6, wherein the mutable indicia can comprise a second indicia, and the plunger of the syringe is provided with at least one of a stopper and the second indicia on the plunger or the stopper, and analysis of the image detects that the first indicia is altered by the movement of the plunger when a condition occurs that is selected from the first indicia being at least partially obscured by the stopper, the first indicia being at least partially obscured by the second indicia, and the first indicia and the second indicia being combined in the image to represent the second state of the syringe.

9. The medical delivery system of claim 8, wherein analysis of the image employs a combination of the first indicia and the second indicia to detect that the spring mechanism has advanced the needle guard plunger and the syringe to retract the needle into the body.

10. The medical delivery system of claim 6, wherein the mutable indicia can comprise a second indicia, and the needle guard plunger of the syringe is provided with the second indicia, and analysis of the image employs a combination of the first indicia and the second indicia to detect that the spring mechanism has advanced the needle guard plunger and the syringe to retract the needle into the body.

11. The medical delivery system of claim 10, wherein analysis of the image comprises determining whether the combination of the first indicia and the second indicia comprises an altered indicia with increased length than the first indicia or the second indicia.

12. The medical delivery system of claim 6, wherein the set of computer-readable instructions are configured to communicate, to another device, the determined first state corresponding to the syringe being unaltered during the pre-delivery state, or the determined second state corresponding to advancement of the needle guard plunger and the syringe to retract the needle into the body.

13. The medical delivery system of claim 6, wherein the set of computer-readable instructions are configured to communicate the determined state of the syringe to another device.

14. A medical delivery system comprising:

a drug delivery device selected from the group comprising a syringe, an autoinjector pen, and a wearable autoinjector, the drug delivery device comprising a mutable indicia that is altered after a designated operation of the drug delivery device selected from the group consisting of removal of a pen cap or needle cap, movement of a plunger or other drive mechanism to dispense a fluid from the drug delivery device, mechanical motion of a component of the drug delivery device, and movement of a drug delivery device component after the fluid is dispensed; and a set of computer-readable instructions that analyze an image of the mutable indicia and assign a first state of the drug delivery device when analysis of the image detects that the mutable indicia is unaltered, and assign a second state of the drug delivery device when analysis of the image detects that the mutable indicia has been altered by the designated operation of the drug delivery device, and stores the assigned states in a memory device, the medical delivery system further comprising a needle guard comprising a needle guard plunger having a plunger cavity to at least partially receive a syringe, and a body having a body cavity to at least partially receive the needle guard plunger, the needle guard plunger having an opening at its proximal end to receive the syringe into the plunger cavity and an opening at its distal end through which a needle of the syringe extends when in a pre-delivery state, the body having a spring mechanism at its distal end that engages the distal end of the needle guard plunger in an energy storage state during the pre-delivery state, the spring mechanism operable in a released energy state to advance the needle guard plunger and the syringe toward a proximal end of the body to retract the needle of the syringe into the body after the syringe has completed a delivery of fluid therefrom;

wherein the mutable indicia comprises a first indicia provided on the body and a second indicia provided on the needle guard plunger, the mutable indicia being assigned by the set of instructions to the first state during the pre-delivery state and being assigned to the second state when it is altered after the spring mechanism advances the needle guard plunger and the syringe to retract the needle into the body.

15. A medical delivery system comprising:

a drug delivery device selected from the group comprising a syringe, an autoinjector pen, and a wearable autoinjector, the drug delivery device comprising a mutable indicia that is altered after a designated operation of the drug delivery device selected from the group consisting of removal of a pen cap or needle cap, movement of a plunger or other drive mechanism to dispense a fluid from the drug delivery device, mechanical motion of a component of the drug delivery device, and movement of a drug delivery device component after the fluid is dispensed; and a set of computer-readable instructions that analyze an image of the mutable indicia and assign a first state of the drug delivery device when analysis of the image detects that the mutable indicia is unaltered, and assign a second state of the drug delivery device when analysis of the image detects that the mutable indicia has been altered by the designated operation of the drug delivery device, and stores the assigned states in a memory device, wherein the drug delivery device is an autoinjector pen and the mutable indicia is provided on at least one of a pen cap removably affixed to the autoinjector pen, a needle removably affixed to the autoinjector pen, a dose window through which a fluid for delivery and a drive mechanism configured to expel the fluid from the autoinjector pen are visible, and a fluid cartridge if the autoinjector pen is reusable.

16. The medical delivery system of claim 15, wherein the mutable indicia is provided on the dose window or on a body of the autoinjector pen and adjacent to the dose window, and the drive mechanism has a rubber seal at its distal end that is translated to dispense the fluid, and the set of computer-readable instructions analyzes one or more images of the mutable indicia, and assigns the first state to the drug delivery device when analysis of the one or more images detects that the mutable indicia is unaltered, and assigns the second state to the drug delivery device when analysis of the one or more images detects a condition selected from the group consisting of the mutable indicia being at least partially obscured by the rubber seal, a change in location of an obscured part of the mutable indicia by the rubber seal, and a change in the mutable indicia relative to a measurement scale provided on the dose window or on the body adjacent resulting from at least one of fluid dispensing or rubber seal movement, and the set of computer-readable instructions is configured to process the captured images of the dose window and determine a dialed dose or the delivered dose.

17. A medical delivery system comprising:

a drug delivery device selected from the group comprising a syringe, an autoinjector pen, and a wearable autoinjector, the drug delivery device comprising a mutable indicia that is altered after a designated operation of the drug delivery device selected from the group consisting of movement of a plunger or other drive mechanism to dispense a fluid from the drug delivery device, mechanical motion of a component of the drug delivery device, and movement of a drug delivery device component after the fluid is dispensed; and a set of computer-readable instructions that analyze an image of the mutable indicia and assign a first state of the drug delivery device when analysis of the image detects that the mutable indicia is unaltered, and assign a second state of the drug delivery device when analysis of the image detects that the mutable indicia has been altered by the designated operation of the drug delivery device, and stores the assigned states in a memory device;

wherein the first state of the drug delivery device is a pre-delivery state, and the second state of the drug delivery device is selected from the group consisting of delivery commenced by movement of the mechanical motion of the component of the drug delivery device, and delivery completed by the mechanical motion of the component of the drug delivery device to an end position; and wherein the set of computer-readable instructions is configured to determine from the altered mutable indicia a state of the drug delivery device selected from the group consisting of a movement distance of the component of the drug delivery device, an amount of fluid remaining in the drug delivery device, and an amount of fluid delivered from the drug delivery device by movement of the component of the drug delivery device.

18. The medical delivery system of claim 17, wherein the set of computer-readable instructions associates and stores in the memory device respective time stamps corresponding to the assigned states.

19. The medical delivery system of claim 17, wherein the set of computer-readable instructions is in a software application stored in a memory of a digital device, and the image is generated by a camera associated with the digital device.

20. The medical delivery system of claim 17, wherein the mutable indicia comprises one or more characteristics selected from the group consisting of a machine-readable code, a barcode, printed indicia, etched indicia, alphanumeric indicia, color-coded indicia, optical indicia, indicia representing a measurement scale, indicia comprising one or more stripes, and indicia comprising one or more shapes.

21. The medical delivery system of claim 17, wherein the mutable indicia is altered by an operation selected from extending the mutable indicia, shortening the mutable indicia, changing an optical property of the mutable indicia, and changing a physical property of the mutable indicia.

22. The medical delivery system of claim 17, wherein the set of computer-readable instructions are configured to communicate the determined first state or second state to another device.

* * * * *